United States Patent [19]
Berg

[11] Patent Number: 6,017,423
[45] Date of Patent: Jan. 25, 2000

[54] SEPARATION OF 3-METHYL-2-PENTENAL FROM N-BUTANOL BY EXTRACTIVE DISTILLATION

[76] Inventor: Lloyd Berg, 1314 S. 3rd Ave., Bozeman, Mont. 59715

[21] Appl. No.: 09/359,731

[22] Filed: Jul. 23, 1999

[51] Int. Cl.[7] .............................. B01D 3/40; C07L 29/84; C07L 45/83
[52] U.S. Cl. ............................ 203/57; 203/58; 203/60; 203/62; 203/64; 203/65; 568/492; 568/913
[58] Field of Search ............................ 203/57, 65, 64, 203/62, 60, 58; 568/492, 913

[56] References Cited

U.S. PATENT DOCUMENTS

| | | |
|---|---|---|
| 3,689,371 | 9/1972 | Kerber et al. ............................... 203/37 |
| 4,054,555 | 10/1977 | Ackermann et al. .................... 568/492 |
| 4,559,111 | 12/1985 | Drake ......................................... 203/57 |
| 4,986,885 | 1/1991 | Driscoll et al. ............................ 203/72 |
| 5,064,508 | 11/1991 | Weber et al. ............................ 568/492 |
| 5,362,918 | 11/1994 | Aizawa et al. ............................. 203/68 |
| 5,756,866 | 5/1998 | Rescalli et al. .......................... 568/913 |

FOREIGN PATENT DOCUMENTS 4346959  12/1992  Japan .

*Primary Examiner*—Virginia Manoharan

[57] ABSTRACT

3-Methyl-2-pentenal cannot be separated from n-butanol by conventioal rectification because of the proximity of their boiling points. 3-methyl-2-pentenal can be readily separated from n-butanol by extractive distillation. Effective agents are 1-methyl-2-pyrrolidinone, 1,4-butanediol and phenol.

1 Claim, No Drawings

SEPARATION OF 3-METHYL-2-PENTENAL FROM N-BUTANOL BY EXTRACTIVE DISTILLATION

FIELD OF THE INVENTION

This invention relates to a method for separating 3-methyl-2-pentenal from n-butanol by extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrees or more higher than the highest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

The usual method of evaluating the effectiveness of extractive distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theoretical stage Requirements.

| Separation Purity, | Relative Volatility | | | | | | | |
|---|---|---|---|---|---|---|---|---|
| Both Products (Mole Fraction) | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

3-Methyl-2-pentenal and n-butanol boil about two degrees apart, have a relative volatility of 1.1 and are difficult to separate by conventional rectification. Table 2 shows that with an agent giving a relative volatilty of 2.7, only twelve actual plates are required.

TABLE 2

Theoretical and Actual Plates Required vs. Relative Volatility for 3-Methyl-2-pentenal - n-Butanol

| Relative Volatility | Theoretical Plates Required At Total Reflux, 99% Purity | Actual Plates Required, 75% Eff. |
|---|---|---|
| 2.7 | 9 | 12 |
| 2.5 | 10 | 14 |
| 2.0 | 12 | 16 |

OBJECTIVE OF THE THE INVENTION

The object of this invention is to provide a process or method of extractive distillation that will enhance the relative volatility of 3-methyl-2-pentenal from n-butanol in their separation in a rectification column. It is a further object of thie invention to identify effective extractve distillation agents that are stable and can be recycled.

SUMMARY OF THE INVENTION

The objects of this invention are to provide a process for the separation 3-methyl-2-pentenal from n-butanol which entails the use of certain organic compounds when employed as the agent in extractive distillation.

DETAILED DESCRIPTION OF THE INVENTION

I have discovered that certain organic compounds will effectively increase the relative volatility between 3-methyl-2-pentenal and n-butanol during rectification when employed as the agent in extractive distillation. They are 3-ethyl phenol, 1,3-butanediol, 1,4-butanediol, butyrolactone, phenol, formamide, 1-methyl-2-pyrrolidinone, ethylene glycol, methyl sulfoxide and dibutyl phthalate.

TABLE 3

Effective Extractive Distillation Agents For Separating 3-Methyl-2-pentenal From n-Butanol

| Compounds | Relative Volatility |
|---|---|
| None | 1.1 |
| 3-Ethyl phenol | 1.7 |
| 1,3-Butanediol | 2.1 |
| 1,4-Butanediol | 2.8 |
| Butyrolactone | 1.7 |
| Phenol | 2.3 |
| Formamide | 2.0 |
| 1-Methyl-2-pyrrolidinone | 2.9 |
| Ethylene glycol | 1.3 |
| Methyl sulfoxide | 1.2 |
| Dibutyl phthalate | 1.85 |

WORKING EXAMPLE

Example 1

Fifty grams of 3-methyl-2-pentenal—n-butanol mixture and fifty grams 1-methyl-2-pyrrolidinone as the extractive distillation agent were charged to a vapor-liquid equilibrium still and refluxed for two hours. The vapor composition was 54.7% 3-methyl-2-pentenal, 30.1% n-butanol; the liquid composition was 30.3% 3-methyl-2-pentenal, 69.7% n-butanol, This is a relative volatility of 2.9.

I claim:

1. A method for recovering 3-methyl-2-pentenal from a mixture of 3-methyl-2-pentenal and n-butanol which consists essentially of distilling a mixture of 3-methyl-2-pentenal and n-butanol in the presence of an extractive distillation agent, recovering the 3-methyl-2-pentenal as overhead product and the n-butanol and the extractive agent as bottoms product, wherein said extractive distillation agent consists essentially of one material selected from the group consisting of 3-ethyl phenol, 1,3-butanediol, 1,4-butanediol, butyrolactone, phenol, formamide, 1-methyl-2-pyrrolidinone, ethylene glycol, methyl sulfoxide and dibutyl phthalate.

\* \* \* \* \*